(12) United States Patent
Pratt et al.

(10) Patent No.: US 8,840,682 B2
(45) Date of Patent: Sep. 23, 2014

(54) OXIDIZING COMPOSITION FOR HAIR

(75) Inventors: Dominic Pratt, Gross-Gerau (DE); Ovidiu Feieriova, Darmstadt (DE)

(73) Assignee: Kao Germany GmbH, Darmstadt (DE)

( * ) Notice: Subject to any disclaimer, the term of this patent is extended or adjusted under 35 U.S.C. 154(b) by 0 days.

(21) Appl. No.: 13/994,897

(22) PCT Filed: Dec. 23, 2011

(86) PCT No.: PCT/EP2011/073945
§ 371 (c)(1), (2), (4) Date: Jun. 17, 2013

(87) PCT Pub. No.: WO2012/089664
PCT Pub. Date: Jul. 5, 2012

(65) Prior Publication Data
US 2013/0269722 A1  Oct. 17, 2013

(30) Foreign Application Priority Data
Dec. 27, 2010 (EP) .................................... 10016084

(51) Int. Cl.
*A61Q 5/08* (2006.01)
*A61K 8/19* (2006.01)
*A61K 8/42* (2006.01)
*A61Q 5/06* (2006.01)
*A61K 8/41* (2006.01)
*A61K 8/22* (2006.01)
*A61Q 5/10* (2006.01)

(52) U.S. Cl.
CPC ... *A61K 8/42* (2013.01); *A61Q 5/08* (2013.01); *A61K 8/19* (2013.01); *A61Q 5/065* (2013.01); *A61K 8/41* (2013.01); *A61K 8/22* (2013.01); *A61Q 5/10* (2013.01)
USPC ............................ 8/101; 8/107; 8/109; 8/111

(58) Field of Classification Search
CPC ............. A61K 8/19; A61K 8/22; A61K 8/41; A61K 8/42; A61Q 5/065; A61Q 5/08; A61Q 5/10
USPC ...................................... 8/101, 107, 109, 111
See application file for complete search history.

(56) References Cited

FOREIGN PATENT DOCUMENTS

| EP | 2 193 780 A2 | 6/2010 | |
|---|---|---|---|
| EP | 2193780 A2 * | 6/2010 | ............... A61K 8/42 |

OTHER PUBLICATIONS

STIC Search Report dated Jul. 31, 2013.*
English translation of the Patent EP 2193780 A2 dated Aug. 2, 2013.*
International Search Report mailed Oct. 31, 2012.

* cited by examiner

*Primary Examiner* — Eisa Elhilo
(74) *Attorney, Agent, or Firm* — Norris Mclaughlin & Marcus PA

(57) ABSTRACT

Present invention relates to an oxidizing composition for keratin fibers especially for human hair with improved lightening effect and therefore, improved coloring and bleaching effects are easily achieved of the compositions applied after mixing with the said composition. Present inventors have surprisingly found out that a composition comprising at least one oxidizing agent and additionally at least one alkalizing agent, at least one carbonate source and at least one urea derivative delivers an improved and homogeneous lightening performance and leaves hair in an improved cosmetically acceptable conditioned status.

12 Claims, No Drawings

OXIDIZING COMPOSITION FOR HAIR

This application is a 371 application of PCT/EP2011/073945 filed Dec. 23, 2011, which claims foreign priority benefit under 35 U.S.C. §119 of European Application No. 10016084.5 filed Dec. 27, 2010.

Present invention relates to an oxidizing composition for keratin fibers especially for human hair with improved lightening effect and, therefore, improved coloring and bleaching effects are easily achieved of the compositions applied after mixing with the said composition.

Lightening of the keratin fibers especially human hair is common practice either for lightening hair color without adding any further color or only for lightening purposes. Such process is very much dependent on the physical status of hair. Healthy hair is stronger and therefore lightened somewhat in lesser extent than that of damaged and usually therefore porous hair under the same conditions. Human hair especially (semi)long hair is usually includes mixture of hair with largely variable in its physical status. Hair especially previously chemically treated hair includes parts varying even more largely in its physical status in terms of hair damage. This brings about performance differences of the lightening compositions used.

Furthermore, hair status after a lightening service is an issue and often additional products must be used in order to achieve a cosmetically acceptable and manageable hair. This is time consuming and uneconomical.

The present invention starts from the above mentioned problems of lightening of keratin fibers especially human hair and aims at providing a composition which lightens hair better and homogeneous and also leaves hair in an improved conditioning status.

Present inventors have surprisingly found out that a composition comprising at least one oxidizing agent and additionally at least one alkalizing agent, at least one carbonate source and at least one urea derivative delivers an improved and homogeneous lightening performance and leaves hair in an improved cosmetically acceptable conditioned status.

Accordingly, the first object of the present invention is an aqueous composition for keratin fibers especially human hair comprising at least one oxidizing agent which further comprises at least one alkalizing agent selected from the compounds according to general structure

wherein $R_1$, $R_2$ and $R_3$ are same or different H, $C_1$-$C_6$ alkyl, $C_1$-$C_6$ monohydroxyalkyl or $C_2$-$C_6$ polyhydroxyalkyl with the condition that at least one of $R_1$, $R_2$ and $R_3$ is a mono or polyhydroxyalkyl,
at least one carbonate source, and
at least one urea or its derivative selected from the compounds according to general structure

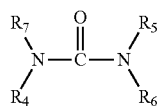

wherein $R_4$ to $R_7$ are same or different H, $C_1$-$C_6$ alkyl, $C_1$-$C_6$ monohydroxyalkyl or $C_2$-$C_6$ polyhydroxyalkyl.

The second object of the present invention is the use of the composition as disclosed above for lightening keratin fibers especially human hair.

Composition of the present invention comprises at least one oxidizing agent. Suitable oxidizing agents are hydrogen peroxide, hydrogen peroxide, urea peroxide, melamin peroxide or perborate salts. The most preferred is hydrogen peroxide. Concentration of at least one oxidizing agent is in the range of 0.1 to 20%, preferably 0.2 to 15%, more preferably 0.5 to 15% and most preferably 1 to 12% by weight, calculated to total of the composition.

All concentrations mentioned within the description refer to the concentration of the respective compound in the composition prior to mixing with any other composition, if necessary, unless otherwise mentioned.

Composition of the present invention comprises at least one alkalizing agent selected from the compounds according to general structure given above. In the preferred embodiment of the present invention, at least one alkanolamine is selected from compounds according to the above general structure wherein $R_1$, $R_2$ and $R_3$ are same or different H, $C_1$-$C_4$ alkyl, $C_1$-$C_4$ monohydroxyalkyl or $C_2$-$C_4$ polyhydroxyalkyl with the condition that at least one of $R_1$, $R_2$ and $R_3$ is a mono or polyhydroxyalkyl.

According to the most preferred embodiment of the present invention at least one alkanolamine is selected from compounds according to the above general formula wherein $R_1$, $R_2$ and $R_3$ are same or different H, $C_2$-$C_4$ alkyl, $C_2$-$C_4$ monohydroxyalkyl or $C_2$-$C_4$ polyhydroxyalkyl with the condition that at least one of $R_1$, $R_2$ and $R_3$ is a mono or polyhydroxyalkyl.

Suitable alkanolamines according to the general formula of above are monoethanolamine, diethanolamine, triethanolamine, monoethanol methylamine, monoethanoldimethylamine, di-ethanol/methylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine and triethanolamine. The most preferred is monoethanolamine.

The concentration of at least one alkanolamine in the compositions varies between 1 and 35%, preferably 1 and 30, more preferably 2.5 and 25 and most preferably 2.5 to 20% by weight calculated to the total composition.

Composition of the present invention comprises at least one carbonate source. Suitable ones are carbonates and bicarbonates salts. Non-limiting examples are ammonium bicarbonate, ammonium carbonate, lithium carbonate, lithium bicarbonate, potassium carbonate, potassium bicarbonate, sodium carbonate and sodium bicarbonate. Preferred are ammonium bicarbonate, ammonium carbonate, potassium carbonate, potassium bicarbonate, sodium carbonate and sodium bicarbonate. More preferred are ammonium bicarbonate, ammonium carbonate, sodium carbonate and sodium bicarbonate and most preferred are ammonium bicarbonate and ammonium carbonate. Particularly ammonium carbonate has found to be excellent in performance.

Concentration of at least one carbonate source is in the range of 0.1 to 20%, preferably 0.2 to 15%, more preferably 0.5 to 12% and most preferably 1 to 10% and particularly 1 to 5% by weight calculated to total of the composition.

Composition of the present invention comprises at least one urea or its derivative selected from the compounds according to the general structure given above. $R_4$ Preferably the $R_4$ to $R_7$ are same or different H, $C_1$-$C_4$ alkyl, $C_1$-$C_4$ monohydroxyalkyl or $C_2$-$C_4$ polyhydroxyalkyl. More preferably the $R_4$ to $R_7$ are same or different H, $C_1$-$C_2$ alkyl, $C_1$-$C_2$ monohydroxyalkyl or $C_2$-$C_4$ polyhydroxyalkyl. Most preferably $R_4$ to $R_7$ are all H.

Suitable non-limiting examples are urea, dimethylol urea, dimethyl urea, hydroxyethyl urea, diethyl urea and monoethanol urea. Most preferred compound is urea.

Concentration of at least one urea and its derivative is in the range of 0.1 and 20%, preferably 0.2 to 15%, more preferably 0.5 to 12% and most preferably 1 to 10% and particularly 1 to 7.5% by weight calculated to total of the composition.

Composition of the present invention comprises preferably at least one oil. Suitable ones are selected from synthetic and natural oils. Suitable synthetic oils are silicone oils either volatile or non-volatile ones such as volatile or non-volatile dimethicone, dimethiconol, polydimethylsiloxane, DC fluid ranges from Dow Corning, cyclosiloxanes such as DC 245 and arylated silicones such as diphenyl dimethicone, diphenylsiloxy phenyl trimethicone, tetramethyl tetraphenyl trisiloxane, triphenyl trimethicone, tetramethly tetraphenyl trisiloxane and trimethyl pentaphenyl trisiloxane. Synthetic oils include mineral oil such as paraffin oil and petrolatum. Further suitable synthetic oils are fatty acid esters such as isopropyl myristate, palmitate, stearate and isostearate, oleyl oleate, iso-cetyl stearate, hexyl laurate, dibutyl adipate, dioctyl adipate, myristyl myristate, oleyl erucate, cetyl palmitate, etc.

Natural oils suitable are such as argan oil, shea butter oil, olive oil, almond oil, avocado oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin and the derivatives thereof.

Concentration of at least one oil in the compositions of the present invention is in the range of 0.1 and 50%, preferably 0.2 to 40%, more preferably 0.5 to 35% and most preferably 1 to 30% and particularly 1 to 25% by weight calculated to total of the composition.

Compositions of the present invention may be used as they are or in combination with one or more dyestuffs and/or in combination with one or more persalts with stringer bleaching effect. Especially in the cases wherein an oxidative dyestuff and/or bleaching persalt are comprised, it is then required that the dyestuffs or bleaching persalts are kept separate until the application onto hair and mixed immediately prior to application with an oxidizing composition of the present invention.

Composition of the present invention comprises at least one hair dye which is selected from oxidative dyes and direct dyes which may be cationic, anionic and neutral.

In principal all oxidative dyes available for hair colouring purposes are suitable within the meaning of the present invention. As a rule, it is possible to incorporate any developing substances known in the sate of the art. Special mention is made of p-phenylenediamine, p-aminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)amino-benzene, 2-(2-hydroxyethyl amino)-5-aminotoluene, 4,4'-diaminodiphenylamine, 4-aminodiphenylamine, 2-amino-5-N,N-diethylaminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetramino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable ones aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethylpyridine, 2-amino-3-hydroxypyridine, 3-amino-2(β-hydroxyethyl amino)-6-methoxypyridine, 2,6-dimethyl amino-5-aminopyridine, 2-di(hydroxyethyl)amino-5-aminopyridine, 2-hydroxyethyl amino-5-aminopyridine, 4-hydroxy-2,5,6-triaminopyrimidine and/or the water-soluble salts thereof.

Within the meaning of the present invention above mentioned developers can as well be present as a mixture of each other.

The total concentration of the dye precursors (developing substances) customarily ranges between 0.001 to 5%, preferably 0.01 to 4% and more preferably 0.05 to 3%, and most preferably 0.1 to 2% by weight, calculated to the total composition, whereby these figures are always related to the proportion of free base.

In a further embodiment of the present invention compositions comprise in addition to at least one oxidative dye precursor at least one coupling substance. As a rule any coupling substance customarily used in oxidative hair colouration area is suitable within the meaning of the present invention. Non-limiting coupling substances, are 5-amino-2-methylphenol, 2-methyl-5-hydroxyethylaminophenol, 2,4,-diamnophenoxyehanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hy-droxyethylamino)benzene, 1-amino-3-[bis(2'-hydroxy-ethyl)amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene and/or 1,3-bis(2,4-diaminophenoxy) propane or the water-soluble salts thereof. One or more of the above mentioned coupler can also be used in a mixture.

In the hair dyeing compositions according to the invention, the coupling substance(s) as reaction partners of the developing substance(s) are present in approximately the same molecular proportions as the developing substances, i.e. in amounts from 0.001 to 5%, preferably 0.01 to 4% and more preferably 0.05 to 3%, and most preferably 0.1 to 2% by weight, calculated to the total composition, whereby these figures always relate to the proportion of free base.

Suitable direct dyes are selected from cationic, anionic, neutral dyes and mixtures thereof as available commercially from various suppliers and used mainly in semi-permanent hair coloration.

One of the suitable direct dyes is cationic dyes. Non-limiting examples are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, and their salts such as chloride, methosulfate, bromide etc. and mixtures thereof.

Further suitable direct dyes are anionic dyes. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and their mixtures.

Further suitable dyes for colouring hair within the meaning of the present invention are those of neutral nitro dyes. Suitable non-limiting examples are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and their mixtures.

Plant dyestuffs may also be used as hair colorant within the meaning of the present invention for example henna (red or black), alkanna root, laccaic acid, indigo, logwood powder, madder root and rhubarb powder, etc.

It should be noted that the above dyestuffs are also suitable for use in mixture. In other words, cationic, anionic and nitro dyes are used in mixture within the meaning of the present invention. When using direct dyes of various categories, their compatibility must be taken into account.

Among the direct dyes cationic and nitro dyes are preferred ones. Most preferred ones are cationic direct dyes.

Concentration of direct dyes in the compositions of the present invention is within the range of 0.001 to 5%, preferably 0.01 to 4% and more preferably 0.05 to 3%, and most preferably 0.1 to 2% by weight, calculated to total composition.

The total concentration of hair dye is preferably in the range of 0.001 to 15%, preferably 0.01 to 10% and more preferably 0.05 to 7.5%, and most preferably 0.1 to 5% by weight, calculated to total composition.

According to the present invention, the composition comprises at least one compound with bleaching and/or highlighting effect in order to achieve stronger bleaching performance on hair. As mentioned above, the bleaching additives must be kept in substantially anhydrous form until application onto hair and are mixed immediately prior to application with an aqueous oxidizing composition of the present invention. Suitable compounds are in general peroxides. Useful as such are in particular persulfates such as sodium and potassium persulfate, ammonium persulfate, earth alkali peroxides such as magnesium peroxide, melamine peroxide or urea peroxide or phtholimidoperoxy-hexanoic acid, and mixtures thereof. The proportion of peroxides is at least 5%, preferably in the range of 20 to 80%, more preferably 25 to 60% and most preferably 30 to 55% by weight, calculated to the total composition prior to mixing with the aqueous oxidizing composition of the present invention.

According to the invention, substantially anhydrous bleaching additive composition can also comprise 0.1% to 10% by weight, calculated to total composition prior to mixing with the aqueous oxidizing composition, at least one ammonium salts. Suitable ammonium salts are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate. Compositions may also comprise mixture or ammonium salts.

Preferred thereof are the ammonium phosphates, such as ammonium dihydrogen phosphate, ammonium hydrogen phosphate, diammonium sodium phosphate, sodium ammonium hydrogen phosphate, ammonium disodium phosphate, as well as ammonium chloride, ammonium sulphate, diammonium hydrogen citrate, ammonium carbonate, ammonium hydrogen carbonate preferably in an amount from 0.1% to 10% by weight, calculated to total composition prior to mixing with the aqueous oxidizing composition.

The total proportion of the compounds with bleaching and/or highlighting effect preferably ranges from 5% to 85%, preferably 20% to 80%, more preferably 25 to 70% and most preferably 30 to 60% by weight calculated to total composition prior to mixing with oxidizing lotion.

Compositions according to the present invention can be in the form of emulsion, solution, dispersion, thickened liquid and/or gel. Emulsion form is preferred.

Composition of present invention can comprise additionally in the base formulation fatty acids with 0 to 3 ethylenic bonds and with fatty acyl chain length of 12 to 22 C atom. Concentration of the fatty acids can be in the range of 0.1 to 10%, preferably 0.1 to 7.5% and most preferably 0.2 to 5% by weight calculated to the total composition, prior to mixing with oxidizing agent. Non-limiting examples are myristic acid, palmitic acid, behenic acid, stearic acid, oleic acid, linoleic acid. The most preferred fatty acid is oleic acid.

Composition of the present invention comprise at least one fatty alcohol or mixture of fatty alcohols with the chain length of 14 to 22 C atoms which may be straight or branched, saturated or unsaturated. Examples to suitable fatty alcohols, without limiting the choice, are myristyl alcohol, cetyl alcohol, stearyl alcohol, behenyl alcohol, oleyl alcohol and cetostearyl alcohol, octyldodecanol. The most preferred is cetostearyl alcohol well known with its trade name Lanette O or as Lanette N in mixture with sodium cetearyl sulfate from Cognis. Total fatty alcohol content should be in the range of 1 to 20% by weight, calculated to total composition priot to mixing with an oxidizing agent.

Compositions according to present invention comprises surfactants selected from anionic, amphoteric (or zwiterionic) and/or cationic surfactants as emulsifier or solubilizer. Cationic surfactants are as well used as hair conditioners in the composition.

The preferred non-ionic emulsifiers are ethoxylated fatty alcohols with an alkyl chain of 12 to 24 C atoms and with number of ethoxyl groups of 2 to 50, preferably 10 to 30. Examples are ceteth-20, seteareth-30, palmeth-20, steareth-20, beheneth-20 etc. These compounds are named according to the fatty alcohol they are originating and number of ethoxyl groups is given at the end.

These compounds are well known emulsifiers and found in any cosmetic ingredient book.

Further suited nonionic surfactants are, especially in mixture with fatty alcohol ethoxylates, for example, long-chain fatty acid mono- and dialkanolamides, such as coco fatty acid mono- or diethanolamide and myristic fatty acid mono or diethanolamide, stearic acid mono or diethanolamide.

Further nonionic surfactants suited again especially in admixture with fatty alcohol ethoxylates mentioned above are alkyl polyglucosides of the general formula

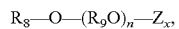

wherein $R_8$ is an alkyl group with 8 to 18 carbon atoms, $R_9$ is an ethylene or propylene group, Z is a saccharide group with 5 to 6 carbon atoms, n is a number from 0 to 10 and x is a number between 1 and 5.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are aminoxides. Such aminoxides are state of the art, for example $C_{12}$-$C_{18}$-alkyl dimethyl aminoxides such as lauryl dimethyl aminoxide, $C_{12}$-$C_{18}$-alkyl amidopropyl or -ethyl aminoxides, $C_{12}$-$C_{18}$-alkyl di(hydroxyethyl) or (hydroxypropyl) aminoxides, or also aminoxides with ethyleneoxide and/or propyleneoxide groups in the alkyl chain. Such aminoxides are on the market, for example, under the trade names "Ammonyx®", "Aromox®" or "Genaminox®".

Anionic surfactants suitable within the scope of the invention are in principal known from the cleansing compositions and may be present in an amount from 0.1 to about 10% by weight, calculated to the total composition prior to mixing with an oxidizing agent. Compatibility of anionic surfactant in the composition should be taken into account when choosing the type and the concentration.

These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates. Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

wherein $R_{10}$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

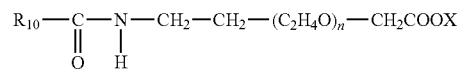

wherein $R_{10}$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants in a mixture.

An overview of the anionic surfactants suitable for the present invention can furthermore be found in the monography of K. Schrader, "Grundlagen and Rezepturen der Kosmetika", $2^{nd}$ Ed. (1989, Hüthig Buchverlag), pp. 595-600 and pp. 683 to 691.

As further surfactant component, the compositions according to the invention can also contain amphoteric or zwitterionic surfactants, for example in an amount from about 0.5% to about 5%, preferably from about 1% to about 2.5% by weight, calculated to the total composition.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Composition can comprise cationic surfactants as emulsifier, solubilizer and/or conditioning ingredients according to the formula,

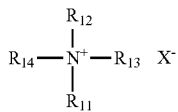

where $R_{12}$ is a saturated or unsaturated, branched or non-branched alkyl chain with 8-22 C atoms or

where $R_{15}$ is saturated or unsaturated, branched or non-branched alkyl chain with 7-21 C atoms and n has typical value of 1-4 or

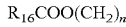

where $R_{16}$ is saturated or unsaturated, branched or non-branched alkyl chain with 7-21 C atoms and n has typical value of 1-4, and
$R_{11}$ is unsaturated or saturated, branched or non-branched alkyl chain with 1-22 C atoms or

or

where $R_{15}$, $R_{16}$ and n are same as above.
$R_{13}$ and $R_{14}$ are lower alkyl chain with 1 to 4 Carbon atoms, and X is typically chloride, bromide, methosulfate.

Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Form the above mentioned surfactants preferred are non-ionic and anionic surfactants and their mixtures.

Total surfactant concentration is in the range of 0.5 to 15%, preferably 1 to 10%, more preferably 1 to 7.5% by weight calculated to total composition prior to mixing with an oxidizing agent.

Composition can also contain cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 2, Polyquaternium 4, Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 67, Polyquaternium 87.

Typical concentration range for any of the cationic conditioners mentioned above can be 0.01-5% by weight, preferably 0.03-2.5% by weight and more preferably 0.05-1.5% by weight.

Composition of the present invention preferably comprise an organopolysiloxane wherein at least one silicium atom is linked to an alkylene group having a hetero-atom, in particular a nitrogen atom, with a poly-(N-acyl alkyleneimine) units of the formula

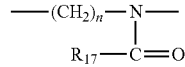

wherein n is a number from 1 to 5 and $R_{17}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

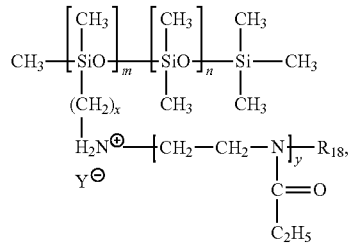

wherein m and n each are numbers from 20 to 10,000, in particular 50 to 7,000, especially 100 to 5,000, x is a number between 1 and 5, preferably 3, and y is a number from 5 to 30, $R_{18}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair compositions according to the invention ranges from 0.05% to 5%, preferably 0.1% to 2.5%, in particular 0.5% to 1.5% by weight, calculated to the total composition.

Compositions according to the present invention can contain organic solvents as penetration enhancers and also as a solubilzers. Examples of such organic solvents are benzyloxy ethanol, benzyl alcohol, phenoxy ethanol, phenoxy isopropanol, methyl phenoxy ethanol, benzyl glycerol, N-benzyl formide, N-methylpyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 20%, preferably 0.5-15%, more preferably 0.5-10%, by weight calculated to the total composition, prior to mixing with oxidizing composition.

Compositions according to the invention may comprise thickening agents. These are, for example, the various cellulose derivatives such as hydroxyalkyl celluloses, e.g. hydroxyethyl cellulose, hydroxypropyl cellulose, hydroxypropyl methyl cellulose, natural polysaccharides such as xanthan gum; guar gum and the alkoxylation products thereof in amounts from 0.1-5%, preferably 0.1-3% and most preferably 0.1-2% by weight calculated to the total composition prior to mixing with oxidizing composition and depending on the desired consistency thereof.

Compositions may further comprise at least one ubiquinone of the formula

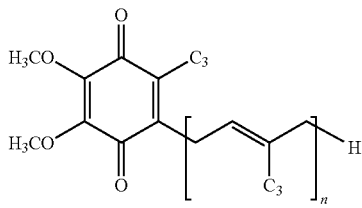

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total composition, prior to mixing with oxidizing composition.

The composition comprises ubiquinone which is preferably selected from the ones where n is a number between 6 and 10 and more preferably it is ubiquinone 50 where n is 10, also known as Coenzyme Q10.

Composition can comprise at least one amino acid. At least one amino acid is comprised at a concentration of 0.01 to 10%, preferably 0.05 to 7.5% and more preferably 0.1 to 5% and most preferably 0.25 to 5% by weight calculated to total of each composition, prior to mixing with oxidizing composition.

Suitable amino acids are glycin, histidine, citrullin, asparagine, alanin, valin, leucin, isoleucin, pyrrolin, tryptophane, phenylalanine, methionine, serine, tyrosine, threonine and gluatamine. Preferably, the amino acid is selected from glycin, histidine, citrullin, asparagine, alanin, valin, leucin, isoleucin, pyrrolin, serine, tyrosine, threonine and gluatamine. More preferably, at least one amino acid is selected from glycin, histidine, asparagine, alanin, valin, leucin, pyrrolin, serine, tyrosine and gluatamine, and most preferably at least one amino acid is selected from glycin, asparagine, alanin, valin, leucin, and serine.

Composition can comprise further ceramide type of compound with the general formula

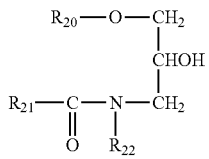

where $R_{20}$ and $R_{21}$ are independent from each other alkyl- or alkenyl group with 10 to 22 carbon atoms, $R_{22}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

pH of the compositions vary in the range of 2 to 12, preferably 5 to 11, more preferably 6 to 10.5 and more preferably 6.8 to 10.5. In case a high lightening effect is looked for, i.e. lightened hair colour is 3 to 4 levels lighter than original hair colour, that high pH values must be preferred. It is the general knowledge of the skilled worker that at alkaline pH the lightening effect is also higher.

As disclosed above in case that dyeing compounds must be comprised in the composition of the present invention it is preferred that the dyestuffs are kept separate until application and offered in a speared composition. Therefore present invention is a kit for lightening and/or colouring keratin fibres wherein it comprises at least two compositions wherein one of them is an aqueous oxidizing composition of the present invention and the other is a composition comprising at least one dyestuff and/or at least one compound with bleaching effect such as persalts.

Furthermore present invention is on process for lightening hair wherein an aqueous composition of the present invention is applied onto hair and rinsed off after processing of 1 to 45 min wherein hair is optionally treated with another composition prior.

Present invention is at the same time on a process for coloring and/or bleaching hair, wherein an aqueous oxidizing composition of the present invention is mixed with another composition comprising either a hair dye or a bleaching compound and applied onto hair and after proceeding of 1 to 45 min rinsed off from hair wherein hair is optionally treated with another composition.

Following examples are to illustrate the invention but not to limit.

EXAMPLE 1

|  | % by weight |
|---|---|
| Monoethanolamine | 5.0 |
| Ammonium bicarbonate | 2.0 |
| Urea | 5.0 |
| Hydrogen peroxide | 6.0 |
| Phosphoric acid/NaOH | q.s to pH 6.8, |
| Water | 100 |

The above composition was prepared by dissolving and mixing the given components in water adjusting the pH immediately prior to application onto hair. It was observed that a composition comprising only peroxide and having otherwise the same pH had considerably less lightening effect. It was furthermore observed that when urea has taken out from the composition, lightening effect was considerably reduced.

Additionally pH of the above composition was adjusted to pH 9.5 and lightening effect was determined on hair streaks. The above given results were confirmed.

EXAMPLE 2

|  | % by weight |
|---|---|
| Octyldodecanol | 1.3 |
| Cetearyl alcohol | 1.0 |
| Oleyl alcohol | 2.6 |
| Paraffin oil | 5.0 |
| Ceteareth-20 | 1.0 |
| Sodium lauryl sulphate | 1.0 |
| Xanthan gum | 1.0 |
| Sodium sulfit | 0.5 |
| Ascorbic acid | 0.2 |

| | % by weight |
|---|---|
| Tetrasodium EDTA | 0.2 |
| Fragrance, preservative | q.s |
| Monoethanolamine | 8.0 |
| Ammonium carbonate | 2.5 |
| Urea | 6.0 |
| Water | q.s. to 100 |

Above composition had a pH of 11 and it was mixed with a composition comprising 12% hydrogen peroxide prior to application onto hair. The mixture had a pH of 9.5 and showed excellent lightening effect. The lightening performance was compared to a composition not comprising monoethanol amine, ammonium bicarbonate and urea but having the same pH (adjusted with ammonia) showed considerably less lightening effect. Especially homogeneity of lightening effect was better with inventive composition compared to the comparative composition.

The above composition was used as the base in the following examples as the base.

EXAMPLE 3

In the composition of the Example 2 the following dyestuff combinations were added. The amount of water was reduced accordingly. The colouring was carried out in the same way as described in Example 2.

| | % by weight |
|---|---|
| Toluene-2,5-diamine sulphate | 0.5 |
| Resorcinol | 0.2 |

Hair streak was coloured homogeneously into a green colour.

EXAMPLE 4

In the composition of the Example 2 the following dyestuff combinations were added. The amount of water was reduced accordingly. The colouring was carried out in the same way as described in Example 2.

| | % by weight |
|---|---|
| Toluene-2,5-diamine sulphate | 0.5 |
| m-aminophenol | 0.25 |

Hair streak was coloured homogeneously into a violet colour.

EXAMPLE 5

In the composition of the Example 2 the following dyestuff combinations were added. The amount of water was reduced accordingly. The colouring was carried out in the same way as described in Example 2.

| | % by weight |
|---|---|
| Toluene-2,5-diamine sulphate | 0.5 |
| 1,3-bis(2,4-diamniophenoxy propane 4 HCl | 0.5 |

Hair streak was coloured homogeneously into a blue colour.

EXAMPLE 6

In the composition of the Example 2 the following dyestuff combinations were added. The amount of water was reduced accordingly. The colouring was carried out in the same way as described in Example 2.

| | % by weight |
|---|---|
| Toluene-2,5-diamine sulphate | 0.5 |
| 2-amino-3-hydroxypyridine | 0.5 |

Hair streak was coloured homogeneously into a reddish violet colour.

EXAMPLE 7

In the composition of the Example 2 the following dyestuff combinations were added. The amount of water was reduced accordingly. The colouring was carried out in the same way as described in Example 2.

| | % by weight |
|---|---|
| Toluene-2,5-diamine sulphate | 0.5 |
| 2-amino-3-hydroxypyridine | 0.5 |
| Basic red 51 | 0.5 |

Hair streak was coloured homogeneously into a red violet colour.

EXAMPLE 8

In the composition of the Example 2 the following dyestuff combinations were added. The amount of water was reduced accordingly. The colouring was carried out in the same way as described in Example 2.

| | % by weight |
|---|---|
| Toluene-2,5-diamine sulphate | 0.5 |
| 2-amino-3-hydroxypyridine | 0.5 |
| HC Blue 17 | 0.5 |

Hair streak was coloured homogeneously into a reddish violet colour.

EXAMPLE 9

The following anhydrous bleaching composition was mixed with the hydrogen peroxide composition given in Example 2 and the emulsion composition of Example 2 in a weight ratio of 1:1:1.

| | |
|---|---|
| Potassium persulfate | 40% by weight |
| Sodium persulfate | 5 |
| Sodium carbonate | 1 |
| Sodium silicate | 10 |
| Diatomaceous Earth | 40 |
| Magnesium sulfate | 4 |

Hair was bleached homogeneously and intensively which was not possible when one of the 3 components of claim 1 was not in the composition.

The invention claimed is:

1. An aqueous composition for keratin fibers comprising at least one oxidizing agent, at least one alkalizing agent selected from the compounds according to general structure

wherein $R_1$, $R_2$ and $R_3$ are same or different H, $C_1$-$C_6$ alkyl, $C_1$-$C_6$ monohydroxyalkyl or $C_2$-$C_6$ polyhydroxyalkyl with the condition that at least one of $R_1$, $R_2$ and $R_3$ is a mono or polyhydroxyalkyl, at least one carbonate source, at least one compound with bleaching effect present at a concentration of between 30-60 wt. %, calculated to the total composition, and at least one urea or urea derivative selected from the compounds according to general structure

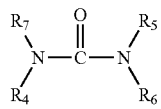

wherein $R_4$ to $R_7$ are same or different H, $C_1$-$C_6$ alkyl, $C_1$-$C_6$ monohydroxyalkyl or $C_2$-$C_6$ polyhydroxyalkyl.

2. The composition according to claim 1 wherein the at least one oxidizing agent is hydrogen peroxide and is present at a concentration of 0.1 to 20% by weight calculated to total of the composition.

3. The composition according to claim 1 wherein the at least one alkalizing agent is selected from the group consisting of monoethanolamine, diethanolamine, triethanolamine, monoethanol methylamine, monoethanoldimethylamine, diethanol/methylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

4. The composition according to claim 3 wherein the at least one alkalizing agent is monoethanolamine.

5. The composition according to claim 1 wherein the at least one carbonate source is selected from ammonium bicarbonate, ammonium carbonate, lithium carbonate, lithium bicarbonate, potassium carbonate, potassium bicarbonate, sodium carbonate and sodium bicarbonate.

6. The composition according to claim 1 wherein the at least one urea or urea derivative is selected from urea, dimethylol urea, dimethyl urea, hydroxyethyl urea, diethyl urea and monoethanol urea.

7. The composition according to claim 6 wherein the urea or urea derivative is urea.

8. The composition according to claim 1 further comprising at least one hair dye.

9. The composition according to claim 8 wherein the hair dye is selected from oxidative dyes and direct dyes.

10. A process for lightening hair comprising applying an aqueous composition according to claim 1 onto hair and rinsing the composition off after processing of 1 to 45 min wherein hair is optionally treated with another composition prior.

11. A process for coloring and/or bleaching hair, comprising mixing an aqueous oxidizing composition according to claim 1 with another composition comprising a hair dye or a bleaching compound and applying the mixture onto hair and rinsing the mixture off the hair after processing for 1 to 45 min rinsed wherein hair is optionally treated with another composition.

12. A kit for lightening and/or colouring keratin fibres comprising at least two compositions wherein one composition is an aqueous oxidizing composition according to claim 1 and the other composition comprises at least one dyestuff and/or at least one compound with bleaching effect.

* * * * *